United States Patent
Dong et al.

(10) Patent No.: US 11,154,487 B2
(45) Date of Patent: *Oct. 26, 2021

(54) ORAL CARE COMPOSITIONS AND METHODS FOR THE SAME

(71) Applicant: Colgate-Palmolive Company, New York, NY (US)

(72) Inventors: Rong Dong, Highland Park, NJ (US); Wei Wang, Plainsboro, NJ (US); Paloma Pimenta, Staten Island, NY (US); Ralph Peter Santarpia, III, Edison, NJ (US); Shira Pilch, Highland Park, NJ (US)

(73) Assignee: Colgate-Palmolive Company, New York, NY (US)

(*) Notice: Subject to any disclaimer, the term of this patent is extended or adjusted under 35 U.S.C. 154(b) by 6 days.

This patent is subject to a terminal disclaimer.

(21) Appl. No.: 16/161,129

(22) Filed: Oct. 16, 2018

(65) Prior Publication Data

US 2020/0113805 A1    Apr. 16, 2020

(51) Int. Cl.
| | | |
|---|---|---|
| *A61K 8/81* | (2006.01) | |
| *A61K 8/21* | (2006.01) | |
| *A61Q 11/00* | (2006.01) | |
| *A61K 8/73* | (2006.01) | |
| *A61K 8/9767* | (2017.01) | |
| *A61K 8/02* | (2006.01) | |

(52) U.S. Cl.
CPC .......... *A61K 8/8152* (2013.01); *A61K 8/0204* (2013.01); *A61K 8/21* (2013.01); *A61K 8/731* (2013.01); *A61K 8/8158* (2013.01); *A61K 8/9767* (2017.08); *A61Q 11/00* (2013.01)

(58) Field of Classification Search
None
See application file for complete search history.

(56) References Cited

U.S. PATENT DOCUMENTS

| | | | |
|---|---|---|---|
| 4,716,035 A * | 12/1987 | Sampathkumar | A61K 8/21 424/52 |
| 7,252,836 B2 | 8/2007 | Brown et al. | |
| 8,883,212 B2 | 11/2014 | Pillai et al. | |
| 9,808,416 B2 | 11/2017 | Georges et al. | |
| 10,596,098 B2 * | 3/2020 | Dong | A61K 8/9767 |
| 2007/0196323 A1 | 8/2007 | Zhang et al. | |
| 2014/0242001 A1 * | 8/2014 | Pillai | A61P 21/02 424/52 |
| 2014/0305461 A1 | 10/2014 | Pimenta et al. | |
| 2015/0257983 A1 | 9/2015 | Lendenmann et al. | |
| 2016/0220472 A1 | 8/2016 | Wang et al. | |
| 2017/0128346 A1 * | 5/2017 | Dong | A61K 8/8158 |
| 2018/0193247 A1 * | 7/2018 | Dong | A61K 8/8147 |
| 2018/0353422 A1 | 12/2018 | Morgan et al. | |

OTHER PUBLICATIONS

Database WPI Week 200436 Thomson Scientific, London, GB; AN 2004-386465 XP002790969, NAM J H (2004).

* cited by examiner

*Primary Examiner* — Brian Gulledge

(57) ABSTRACT

A film forming composition and methods for preventing acid erosion of teeth and preventing the formation of caries on teeth are disclosed. The film forming composition may include a hydrophobic copolymer, a fluoride compound, and an orally acceptable solvent. The film forming composition may also include a cellulose derivative, a rosin, a fluoride compound, and an orally acceptable solvent.

12 Claims, No Drawings

ORAL CARE COMPOSITIONS AND METHODS FOR THE SAME

BACKGROUND

Conventional oral care products are often utilized to deliver fluoride to surfaces of the oral cavity to thereby prevent the formation of caries. For example, fluoride containing toothpastes and mouthwashes are often utilized to deliver or apply fluoride to surfaces of teeth, thereby preventing the formation of caries. The efficacy of fluoride in preventing the formation of caries, however, is partially determined by the ability of the fluoride to maintain contact with the surfaces of the teeth. As such, the efficacy of fluoride delivered to surfaces of the teeth via conventional oral care products (e.g., mouthwashes and toothpastes) is generally unsatisfactory, as the fluoride is often easily removed from the teeth by either physical or chemical processes. For example, fluoride on the surfaces of the teeth may be physically removed by chewing and/or chemically removed by prolonged exposure to the varying temperatures and pH levels of the foods and drinks we consume.

In view of the foregoing, tooth varnish compositions including fluoride were developed to provide relatively longer contact between fluoride and the surfaces of the teeth. While conventional tooth varnish compositions incorporating fluoride demonstrate relatively increased efficacy in preventing the formation of caries as compared to conventional oral care products, they are often highly viscous and slow to dry, which results in the formation of a tacky or sticky coating, which is unpleasant and undesirable. Further, conventional tooth varnish compositions may often utilize natural resins that tend to form relatively thick films having a yellowish tint, which may make the teeth appear stained.

What is needed, then, are improved oral care products and film forming compositions thereof, and methods for preventing the formation of caries that address these and other drawbacks of conventional film forming compositions.

BRIEF SUMMARY

This summary is intended merely to introduce a simplified summary of some aspects of one or more implementations of the present disclosure. Further areas of applicability of the present disclosure will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing a film forming composition for preventing the formation of caries on teeth. The film forming composition may include a hydrophobic copolymer, a fluoride compound, and an orally acceptable solvent.

In at least one implementation, the hydrophobic copolymer may include an acrylate, optionally, the hydrophobic copolymer is an acrylate/octylacrylamide copolymer. In another implementation, the acrylate/octylacrylamide copolymer is 2-propenoic acid, 2-methyl-, 2-methylpropyl ester, polymer with 2-propenoic acid and N-(1,1,3,3-tetramethylbutyl)-2-propenamide.

In at least one implementation, the fluoride compound may be or include a soluble salt of a fluoride ion.

In at least one implementation, the fluoride compound may include one or more of sodium fluoride, potassium fluoride, calcium fluoride, zinc fluoride, zinc ammonium fluoride, lithium fluoride, ammonium fluoride, stannous fluoride, and stannous fluorozirconate. In at least one implementation, the fluoride compound includes sodium fluoride.

In at least one implementation, the orally acceptable solvent may include one or more of ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, and benzyl alcohol. In a preferred implementation, the orally acceptable solvent includes ethanol.

In at least one implementation, the film forming composition may further include an adhesive. In at least one implementation, the adhesive may include one or more of a polyvinyl acetaldehyde, a polyvinyl alcohol, a polyvinyl acetate, a poly(ethylene oxide), a polyacrylate, a polyvinylpyrolidone, a polyvinylpyrolidone/vinyl acetate copolymer, a polyoxyethylene/polyoxopropylene block copolymer, and a silicone resin. In at least one implementation, the adhesive is a rosin.

The foregoing and/or other aspects and utilities embodied in the present disclosure may be achieved by providing a film forming composition for preventing the formation of caries on teeth. The film forming composition may include a cellulose derivative, a rosin, a fluoride compound, and an orally acceptable solvent.

In at least one implementation, the cellulose derivative may include an alkyl cellulose ether, preferably, the cellulose derivative includes ethyl cellulose.

In at least one implementation, the cellulose derivative is the ethyl cellulose, and the ethyl cellulose includes an average substitution value of about 2.25 to about 2.60 ethoxyl groups per anhydroglucose unit.

In at least one implementation, the rosin is at least partially hydrogenated. In another implementation, the rosin is fully hydrogenated.

In at least one implementation, the fluoride compound may be a soluble salt of a fluoride ion.

In at least one implementation, the fluoride compound may include one or more of sodium fluoride, potassium fluoride, calcium fluoride, zinc fluoride, zinc ammonium fluoride, lithium fluoride, ammonium fluoride, stannous fluoride, and stannous fluorozirconate. In another implementation, the fluoride compound may include sodium fluoride.

The foregoing and/or other aspects and utilities embodied in the present disclosure may be achieved by providing a method for preparing any one of the film forming composition disclosed herein, the method may include contacting the acrylate/octylacrylamide copolymer, the fluoride compound, and the orally acceptable solvent with one another.

The foregoing and/or other aspects and utilities embodied in the present disclosure may be achieved by providing a method for preparing any one of the film forming composition disclosed herein, the method may include contacting the cellulose derivative, the rosin, the fluoride compound, and the orally acceptable solvent with one another.

The foregoing and/or other aspects and utilities embodied in the present disclosure may be achieved by providing a method for preventing acid erosion on surfaces of teeth, the method include contacting the surfaces of the teeth with any one of the film forming compositions disclosed herein.

The foregoing and/or other aspects and utilities embodied in the present disclosure may be achieved by providing a method for preventing the formation of caries on teeth, the method may include contacting the teeth with any one of film forming composition disclosed herein.

Further areas of applicability of the present disclosure will become apparent from the detailed description provided hereinafter. It should be understood that the detailed description and specific examples, while indicating some typical aspects of the disclosure, are intended for purposes of illustration only and are not intended to limit the scope of the disclosure.

DETAILED DESCRIPTION

The following description of various typical aspect(s) is merely exemplary in nature and is in no way intended to limit the disclosure, its application, or uses.

As used throughout this disclosure, ranges are used as shorthand for describing each and every value that is within the range. It should be appreciated and understood that the description in a range format is merely for convenience and brevity, and should not be construed as an inflexible limitation on the scope of any embodiments or implementations disclosed herein. Accordingly, the disclosed range should be construed to have specifically disclosed all the possible subranges as well as individual numerical values within that range. As such, any value within the range may be selected as the terminus of the range. For example, description of a range such as from 1 to 5 should be considered to have specifically disclosed subranges such as from 1.5 to 3, from 1 to 4.5, from 2 to 5, from 3.1 to 5, etc., as well as individual numbers within that range, for example, 1, 2, 3, 3.2, 4, 5, etc. This applies regardless of the breadth of the range All references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

The present inventors have surprisingly and unexpectedly discovered that film forming compositions including a fluoride compound and either a hydrophobic polymer (e.g., a acrylate/octylacrylamide copolymer) or a combination of a rosin and a derivative of cellulose (e.g., an alkyl ether of cellulose) exhibit relatively greater durable than commercially available film forming compositions. It has also been surprisingly and unexpectedly discovered that the film forming compositions including a fluoride compound and either a hydrophobic polymer (e.g., a acrylate/octylacrylamide copolymer) or a combination of a rosin and a derivative of cellulose (e.g., an alkyl ether of cellulose) exhibit relatively greater anti-caries effect or relatively greater efficacy for preventing the formation of caries than commercially available film forming compositions. Without being bound by theory, the present inventors believe the balance between the hydrophilicity and hydrophobicity of the film forming composition or the film formed therefrom may provide the surprisingly and unexpected results. For example, the films formed from the film forming compositions disclosed herein exhibit sufficient hydrophilicity to allow aqueous solutions, such as saliva, to traverse therethrough to deliver fluoride ions to surfaces of the teeth while exhibiting sufficient hydrophobicity to maintain durability for prolonged periods of time (e.g., at least 5 min, at least 10 min, at least 30 min, at least 45 min, at least 1 hr, at least 2 hrs, at least 5 hrs, at least 10 hrs, at least 15 hrs, at least 20 hours, at least 1 day, etc.). As further demonstrated herein, the balance of the hydrophilicity and the hydrophobicity allow the films formed from the film forming compositions to exhibit relatively greater durability as compared to conventional films. Further, the balance of the hydrophilicity and the hydrophobicity allow the films formed from the film forming compositions to exhibit relatively greater delivery of fluoride than conventional films, even when including lower concentrations of fluoride.

Compositions

Compositions disclosed herein may be or include an oral care product or a film forming composition thereof. For example, the compositions disclosed herein may be an oral care product including the film forming composition, or the film forming composition thereof. In at least one implementation, the film forming composition may include one or more hydrophobic polymers and one or more fluorides or fluoride compounds. For example, the film forming composition may include an acrylate/octylacrylamide copolymer and a fluoride compound. In another implementation, the film forming composition may include a fluoride compound and a combination of a rosin and a derivative of cellulose. For example, the film forming composition may include a fluoride compound and a combination of a rosin and an alkyl ether of a cellulose (e.g., ethylcellulose). As further described herein, the film forming compositions and/or one or more components thereof may be capable of or configured to deliver fluoride to surfaces of the oral cavity. For example, the film forming compositions and/or one or more components thereof may be configured to deliver fluoride to surfaces of teeth in a sustained manner to thereby provide an anti-caries effect on the teeth.

Hydrophobic Polymers

The one or more hydrophobic polymers of the film forming composition may be or include, but are not limited to, hydrophobic film forming polymers, such as hydrophobic film forming polymers having functional groups with properties that provide relatively increased adhesion to surfaces of the oral cavity (e.g., surfaces of teeth). Illustrative functional groups may include, but are not limited to, carboxyl groups, phosphate groups, hydroxyl groups, amines, disulfides, nitro groups, or the like, and combinations thereof.

In at least one implementation, the hydrophobic polymer may be or include a copolymer. For example, the hydrophobic polymer may be or include a carboxylated acrylic copolymer. In another example, the hydrophobic polymer may be a copolymer of octylacrylamide and one or more monomers, where the one or more monomers may include one or more of acrylic acid, methacrylic acid, and any one or more simple esters thereof. In yet another example, the hydrophobic polymer may be a polymer formed from octylacrylamide, t-butylaminoethyl methacrylate, and one or more monomers of acrylic acid, methacrylic acid, or any one or more simple esters thereof. Illustrative carboxylated acrylic copolymers may be or include, but are not limited to, those sold under the trade names DERMACRYL®, AMPHOMER®, BALANCE®, and VERSACRYL®, which are commercially available from AkzoNobel Company, Surface Chemistry of Amsterdam, Netherlands. For example, the carboxylated acrylic copolymers may be or include, but are not limited to, AMPHOMER® 4961, AMPHOMER® HC, DERMACRYL® 2.0, RESYN™ XP, a hydrophobic copolymer selected from octylacrylamide/acrylates/butylaminoethyl methacrylate copolymer, such as AMPHOMER® LV-71, AMPHOMER®, AMPHOMER® EDGE™, BALANCE® 47, or the like, and combinations thereof, all of which are commercially available from AkzoNobel Company, Surface Chemistry of Amsterdam, Netherlands. The hydrophobic copolymer may be selected from VA/butyl maleate/isobornyl acrylate copolymer, such as ADVANTAGE™ PLUS from Ashland Global Specialty Chemicals Inc. of Covington, Ky. The hydrophobic copolymer may be selected from acrylates/t-butylacrylamide copolymer, such as ULTRAHOLD® STRONG and ULTRAHOLD®8 from BASF SE of Ludwigshafen, Germany. The hydrophobic copolymer may be selected from acrylates/dimethylaminoethyl methacrylate copolymer, such as the EUDRAGIT® range of polymers from Evonik Industries of Essen, Germany, such as EUDRAGIT® E100, EUDRAGIT® E PO, EUDRAGIT® RS 100, EUDRAGIT® RS PO, EUDRAGIT® RL PO, EUDRAGIT® RL 100, or the like, and combinations thereof. The hydrophobic copolymer may be selected from polyvinylpyrrolidone/vinyl acetate, such as the PVP/VA series of polymers from Ashland Global Specialty Chemicals Inc. of Covington, Ky. The hydrophobic copolymer may be selected from triacontanyl PVP, such as GANEX™ WP-660 from Ashland Global Specialty Chemicals Inc. of Covington, Ky. The hydrophobic copolymer may be selected from at least one of octylacrylamide/acrylates/butylaminoethyl methacrylate copolymer, VA/butyl maleate/isobornyl acrylate copolymer, acrylates/t-butylacrylamide copolymer, polyvinylpyrrolidone/vinyl acetate copolymer, triacontanyl PVP copolymer, acrylates/dimethylaminoethyl methacrylate copolymer, or mixtures thereof. In an preferred implementation, the hydrophobic polymer may be a copolymer of 2-Propenoic acid, 2-methyl-, 2-methylpropyl ester, polymer with 2-propenoic acid and N-(1,1,3,3-tetramethylbutyl)-2-propenamide or 2-propenoic acid, 2-methyl-, 2-methylpropyl ester, 2-propenoic acid, N-(1,1,3,3-tetramethylbutyl)-2-propenamide copolymer (CAS 129702-02-9). For example, the hydrophobic polymer may be or include, but is not limited to, DERMACRYL® 79, which is commercially available from AkzoNobel Company, Surface Chemistry of Amsterdam, Netherlands.

The amount or concentration of the one or more hydrophobic polymers present in the oral care product or the film forming composition thereof may vary widely. In at least one implementation, the amount of the one or more hydrophobic polymers present may be from about 1 weight % to about 50 weight %, based on a total weight of the oral care product or the film forming composition thereof. For example, the amount of the one or more hydrophobic polymers present may be from about 1 weight %, about 5 weight %, about 10 weight %, about 15 weight %, about 20 weight %, or about 25 weight % to about 30 weight %, about 35 weight %, about 40 weight %, about 45 weight %, or about 50 weight %. In another example, the amount of the one or more hydrophobic polymers present may be from about 1 weight % to about 50 weight %, about 5 weight % to about 45 weight %, about 10 weight % to about 40 weight %, about 15 weight % to about 35 weight %, about 20 weight % to about 30 weight %, or about 22.5 to about 28.5, or about 25 weight %. In at least one implementation, the amount of the one or more hydrophobic polymers present may be from about 10 weight % to about 30 weight %, based on a total weight of the oral care product or the film forming composition thereof. For example, the amount of the one or more hydrophobic polymers present may be from about 10 weight %, about 12 weight %, about 14 weight %, about 16 weight %, about 18 weight %, about 19 weight %, or about 19.5 weight % to about 20.5 weight %, about 21 weight %, about 22 weight %, about 24 weight %, about 26 weight %, about 28 weight %, or about 30 weight %, based on a total weight of the oral care product or the film forming composition thereof. In another example, the amount of the one or more hydrophobic polymers present may be from about 10 weight % to about 30 weight %, about 12 weight % to about 28 weight %, about 14 weight % to about 26 weight %, about 16 weight % to about 24 weight %, about 18 weight % to about 22 weight %, about 19 weight % to about 21 weight %, or about 19.5 weight % to about 20.5 weight %, based on a total weight of the oral care product or the film forming composition thereof. In a preferred implementation, the amount of the one or more hydrophobic polymers present may be from about 19 weight % to about 21 weight %, about 19.5 weight % to about 20.5 weight %, or about 20 weight %, based on a total weight of the oral care product or the film forming composition thereof.

Fluoride or Fluoride Compounds

The oral care product or the film forming composition thereof may include one or more fluorides or fluoride compounds. As used herein, the expression "fluoride" or "fluoride compound" may refer to a source of fluoride and/or compounds capable of or configured to provide fluoride ions. Illustrated fluorides may be or include, but are not limited to, soluble salts of the fluoride ion, such as sodium fluoride, potassium fluoride, calcium fluoride, zinc fluoride, zinc ammonium fluoride, lithium fluoride, ammonium fluoride, stannous fluoride, stannous fluorozirconate, complex fluorides, monofluorophosphates and salts thereof (e.g., sodium monofluorophosphate or potassium monofluorophosphate), laurylamine hydrofluoride, diethylaminoethyloctoylamide hydrofluoride, didecyldimethylammonium fluoride, cetylpyridinium fluoride, dilaurylmorpholinium fluoride, sarcosine stannous fluoride, glycine potassium fluoride, glycine hydrofluoride, amine fluorides, or the like, and mixtures or combinations thereof. In a preferred implementation, the fluoride is sodium fluoride.

The amount or concentration of the one or more fluoride compounds present in the oral care product or the film forming composition thereof may vary widely. In at least one implementation, the fluoride compounds may be presented in an amount capable of or configured to provide fluoride ions in an amount of from about 100 ppm to about 50,000 ppm. For example, the fluoride compounds may be presented in an amount capable of or configured to provide fluoride ions in an amount of from about 100 ppm, about 500 ppm, about 1,000 ppm, about 5,000 ppm, or about 10,000 ppm to about 15,000 ppm, about 20,000 ppm, about 25,000 ppm, about 30,000 ppm, about 35,000 ppm, about 40,000 ppm, about 45,000 ppm, or about 50,000 ppm. In another example, the fluoride compounds may be presented in an amount capable of or configured to provide fluoride ions in an amount of at least 100 ppm, at least 500 ppm, at least 1,000 ppm, at least 5,000 ppm, at least 10,000 ppm, at least 15,000 ppm, at least 20,000 ppm, at least 25,000 ppm, or at least 30,000 ppm. In a preferred implementation, the fluoride compounds are present in an amount sufficient to provide from about 500 ppm to about 30,000 ppm, more preferably about 1,000 ppm to about 23,000 ppm, or about 1,100 ppm to about 22,600 ppm. It should be appreciated that the exact weight percentage of the fluoride compound in the film forming composition may be at least partially determined by the stoichiometric properties of the varying fluoride compounds. In an exemplary implementation, the fluoride compound is sodium fluoride and is present in an amount of from about 0.5 weight %, about 1 weight %, about 1.5 weight %, about 2 weight %, about 2.5 weight %, about 3 weight %, about 3.5 weight %, about 4 weight %, or about 4.5 weight % to about 5 weight %, about 6.5 weight %, about 7 weight %, about 7.5 weight %, about 8 weight %, or about 8.5 weight %. In a preferred implementation, the sodium fluoride is present in an amount of from about 4 weight % to about 6 weight %, or about 5 weight %. In another preferred implementation, the sodium fluoride is present in an amount of from about 0.5 weight % to about 1.5 weight %, about 1 weight %, or about 1.11 weight %.

Rosin

The oral care product or the film forming composition thereof may include one or more rosins. In at least one implementation, the one or more rosins may be at least partially, hydrogenated. The one or more rosins may be completely or fully hydrogenated. Hydrogenated rosins may be rosin acids or resin acids that have at least some of their carbon-carbon double bonds hydrogenated. It should be appreciated that the relatively greater degree in which the rosins are hydrogenated, the more colorless they appear to the human eye. Accordingly, in at least one implementation, the oral care product or the film forming composition thereof may include a fully hydrogenated rosin that may be transparent or substantially transparent.

Illustrative rosins may be or include, but are not limited to, rosins from the class of rosins known in the art as the colophonium class. Members of the colophonium class are non-synthetic naturally-derived sticky resins (e.g., typically derived from various species of pine). Colophonium may include a substantial fraction of resin acid components that are isomeric with abietic acid ($C_{20}H_{30}O_2$). Examples of colophonium may also include dihydrobietic acid ($C_{20}H_{32}O_2$) and/or dehydroabietic acid ($C_2H_{28}O_2$). Colophonium may range from black to substantially colorless, although resins from this class may typically be pale yellow to amber in color and have a density of about 1.07 to about 1.09 g/cm$^3$. Various materials that are individually referred to as "colophonium" include Canadian balsam, Olibanum balsam, Elemi resin, Opopanax resin, loin balsam, Peruvian balsam, and POLY-PALE™ resin, which is a partially dimerized rosin commercially available from Eastman Chemical Company of Kingsport, Tenn. Illustrative rosins may also be or include, but are not limited to, wood rosin, gum rosin, tall oil rosin and mixtures thereof. The rosins may be in a crude state or a refined state.

In a preferred implementation the one or more rosins of the film forming composition, when present, may be or include, but is not limited to, FORAL™ AX-E, a fully hydrogenated tree rosin that has been distilled and dimerized, which is commercially available from Eastman Chemical Company. FORAL™ AX-E is nearly colorless and in some implementations is more stable than colophonium components. FORAL™ AX-E resists oxidation and retains its substantially colorless characteristics over time. Other suitable commercially available rosins include STAYBELITE™ Resin-E, a partially hydrogenated rosin available from Eastman Chemical Company, which also exhibits good oxidation resistance and pale color. Additional suitable commercially available rosins include PAMITE™ (tall oil rosin), DYMEREX™ (dimerized rosin), POLYSTIX® 90 (partially dimerized rosin), DRESINATE™ (rosin soap) and PERMALYN™ NC-11 (noncrystalline rosin), all of which are commercially available from Eastman Chemical Company.

The amount or concentration of the one or more rosins present in the oral care product or the film forming composition thereof may vary widely. In at least one implementation, the amount of the rosins present in the film forming composition may be from about 1 weight % to about 9 weight %, based on a total weight of the oral care product or the film forming composition thereof. For example, the amount of the rosins present in the film forming composition may be from about 1 weight %, about 2 weight %, about 3 weight %, about 4 weight %, or about 4.5 weight % to about 5.5 weight %, about 6 weight %, about 7 weight %, about 8 weight %, or about 9 weight %, based on a total weight of the oral care product or the film forming composition thereof. In another example, the amount of the rosins present in the film forming composition may be from about 1 weight % to about 9 weight %, about 2 weight % to about 8 weight %, about 3 weight % to about 7 weight %, about 4 weight % to about 6 weight %, or about 4.5 weight % to about 5.5 weight %. In a preferred implementation, the amount of the rosins present may be from about 4 weight % to about 6 weight %, about 4.5 weight % to about 5.5 weight %, or more preferably about 5 weight %.

Derivative of Cellulose

The oral care product or the film forming composition thereof may include one or more derivatives of cellulose or cellulose derivatives. The cellulose derivatives may be or include, but is not limited to, an alkyl cellulose ether. As used herein, the expression "alkyl cellulose ether" may refer to a lower alkyl ether of cellulose, such as an ethyl cellulose. In a preferred implementation, the cellulose derivative is ethyl cellulose. The degree of ethoxylation and/or the viscosity of the ethyl cellulose may vary. For example, the ethyl cellulose may have a degree of ethoxylation of about 45% to about 50% and a viscosity of about 3 cP to about 70 cP (5% solution at 25° C. measured in a Ubbelohde viscometer). In another example, the ethyl cellulose may have an average substitution value of about 2.25 to about 2.60 ethoxyl groups per anhydroglucose unit, or about 44% to about 52% ethoxyl content. In yet another example, the ethyl cellulose may have an average substitution value of about 2.46 to about 2.58 ethoxyl groups per anhydroglucose unit, corresponding to an ethoxyl content of about 48% to about 49.5%. Illustrative ethyl celluloses may be or include, but are not limited to, AQUALON® N100 ethyl cellulose, commercially available from Hercules Inc. of Wilmington, Del., ETHOCEL® Standard 100, ETHOCEL™ E7, ETHOCEL™ E22, ETHOCEL™ E50, or the like, and mixtures thereof, all of which are commercially available from the Dow Corning Company.

The amount or concentration of the cellulose derivatives present in the oral care product or the film forming composition thereof may vary widely. In at least one implementation, the amount of the cellulose derivatives present in the film forming composition may be from about 1 weight % to about 50 weight %, based on a total weight of the oral care product or the film forming composition thereof. For example, the amount of the cellulose derivatives present in the film forming composition may be from about 1 weight %, about 5 weight %, about 10 weight %, about 15 weight %, about 20 weight %, or about 25 weight % to about 30 weight %, about 35 weight %, about 40 weight %, about 45 weight %, or about 50 weight %. In another example, the amount of the cellulose derivatives present in the film forming composition may be from about 1 weight % to about 50 weight %, about 5 weight % to about 45 weight %, about 10 weight % to about 40 weight %, about 15 weight % to about 35 weight %, about 20 weight % to about 30 weight %, or about 22.5 to about 28.5, or about 25 weight %. In another implementation, the amount of the cellulose derivatives present in the film forming composition may be from about 10 weight % to about 16 weight %. For example, the amount of the cellulose derivatives present in the film forming composition may be from about 10 weight %, about 11 weight %, about 12 weight %, or about 12.5 weight % to about 13.5 weight %, about 14 weight %, about 15 weight %, or about 16 weight %, based on a total weight of the oral care product or the film forming composition thereof. In another example, the amount of the cellulose derivatives present in the film forming composition may be from about 10 weight % to about 16 weight %, about 11 weight % to about 15 weight %, about 12 weight % to about 14 weight %, or about 12.5 weight % to about 13.5 weight %. In a preferred implementation, the amount of the cellulose derivative, such as ethyl cellulose, present in the film forming composition may be from about 12 weight % to about 14 weight %, or about 13 weight %.

Adhesive or Adhesion Enhancing Agent

In at least one implementation, the oral care product or the film forming composition thereof may optionally include one or more adhesives configured to improve, maintain, and/or facilitate the adhesion of the film formed from the film forming composition to surfaces of the oral cavity. The one or more adhesives may also be configured to increase the hydrophobicity of the film formed from the film forming composition, thereby allowing the film to withstand external challenges, such as abrading, rubbing, or brushing.

Illustrative adhesives may be or include, but are not limited to, alkyd resins, polyvinyl acetaldehydes, polyvinyl alcohols, polyvinyl acetates, polyethylene oxide), polyacrylates, ketone resins, polyvinylpyrolidone, polyvinylpyrolidone/vinyl acetate copolymer, polyethylene glycols of 200 to 1000 molecular weight, polyoxyethylene/polyoxopropylene block copolymers (Polyox), silicon resins, or the like, and mixtures or combinations thereof. In at least one implementation, the one or more adhesives may include siloxane polymers, which are also generally known in the art as "silicone" polymers. Illustrative silicone-based hydrophobic polymers may be or include, but are not limited to, polyorganosiloxane, polydiorganosiloxane, and the like, and combinations thereof. In at least one implementation, the adhesion enhancing agent includes at least one silicon pressure sensitive adhesive (PSA). Such PSAs may be pressure sensitive hydrophobic polymers specifically designed for pharmaceutical use and are permeable to many drug compounds and find application for the transdermal application of various compounds. In some implementations, the silicone polymers are the copolymer product of mixing a silanol terminated polydiorganosiloxane, such as polydimethyl siloxane, with a silanol-containing silicone resin, whereby the silanol groups of the polydiorganosiloxane undergo a condensation reaction with the silanol groups of the silicone resin such that the polydiorganosiloxane is lightly cross-linked by the silicone resin (that is, the polydiorganosiloxane chains are bonded together through the resin molecules to give chain branching and entanglement and/or a small amount of network character) to form the silicone hydrophobic polymers. In at least one implementation, the adhesion enhancing agents are available under the trade name BIO-PSA from the Dow Corning Company of Midland, Mich. The modification of a ratio of silicone resin to polydiorganosiloxane modifies the tackiness of the polymer. This ratio may be in the range of about 70:30 to about 50:50. For example, the BIO-PSA silicone commercially available from Dow-Corning is available in varying silicone resin to silicone polymer ratios, namely, 65/35 (low tack), 60/40 (medium tack), and 55/45 (high tack). Such a polyorganosiloxane PSA is available dissolved in either ethyl acetate solvent or dimethicone. In at least one implementation, the adhesion enhancing agent may include Silicone Adhesive 8-7016, commercially available from Dow Corning Corporation of Midland, Mich.

In some embodiments, the adhesive is a natural resin. Illustrative natural resins may be or include, but are not limited to, shellac, rosins, or the like, and mixtures or combinations thereof. Shellac is commercially available and may be provided with a solvent (e.g. ethanol). One such commercially available shellac, known as Refined Pharmaceutical Glaze, is available from Mantrose-Haeuser Co., Inc. of Westport, Conn.

The amount or concentration of the adhesion enhancing agents present in the oral care product or the film forming composition thereof may vary widely. The amount of the adhesion enhancing agents present in the film forming composition may be from about 1 weight % to about 5 weight %. For example, the amount of the adhesion enhancing agents present in the film forming composition may be from about 1.0 weight %, about 1.5 weight %, about 2.0 weight %, about 2.5 weight %, or about 3.0 weight % to about 3.5 weight %, about 4.0 weight %, about 4.5 weight %, or about 5.0 weight %. In another example, the amount of the adhesion enhancing agents present in the film forming composition may be from about 1.0 weight % to about 5.0 weight %, about 1.5 weight % to about 4.5 weight %, about 2.0 weight % to about 4.0 weight %, or about 2.5 weight % to about 3.5 weight %. In yet another example, the amount of the adhesion enhancing agents present in the film forming composition may be greater than or equal to greater than or equal to 1.0 weight %, greater than or equal to 1.5 weight %, greater than or equal to 2.0 weight %, greater than or equal to 2.5 weight %, greater than or equal to 3.0 weight %, greater than or equal to 3.5 weight %, greater than or equal to 4.0 weight %, or greater than or equal to 4.5 weight %. In another example, the amount of the adhesion enhancing agents present in the film forming composition may be less than or equal to 1.0 weight %, less than or equal to 1.5 weight %, less than or equal to 2.0 weight %, less than or equal to 2.5 weight %, less than or equal to 3.0 weight %, less than or equal to 3.5 weight %, less than or equal to 4.0 weight %, less than or equal to 4.5 weight %, or less than or equal to 5.0 weight %. In a typical implementation, the amount of the adhesion enhancing agents present in the film forming composition is about 3.0 weight %.

In an exemplary implementation, the oral care product or the film forming composition thereof is free or substantially free from any adhesives and/or rosins. For example, the oral care product or the film forming composition thereof may explicitly exclude any additional adhesives and/or rosins. As used herein, "free" or "substantially free" may refer to a composition, component, or phase that contains less than 10.0 wt %, less than 5.0 wt %, less than 3.0 wt %, less than 1.0 wt %, less than 0.1 wt %, less than 0.05 wt %, less than 0.01 wt %, less than 0.005 wt %, or less than 0.0001 wt % based on a total weight of the oral care product or the film forming composition thereof. In at least one implementation, the oral care product or the film forming composition thereof may exclude any one or more components capable of or configured to enhance adhesion of the oral care product or the film forming composition to surfaces of the teeth. For example, the film forming composition may consist essentially of the hydrophobic polymer, the fluoride compound, and an orally acceptable solvent.

Thickening System

In at least one implementation, the oral care product or the film forming composition thereof may optionally include a thickening system having one or more thickeners. The one or more thickeners may be any orally acceptable thickener or thickening agent. Illustrative thickeners may be or include, but are not limited to, colloidal silica, fumed silica, a cross-linked polyvinylpyrrolidone (PVP) polymer, cross-linked polyvinylpyrrolidone (PVP), and the like, and mixtures or combinations thereof. The thickening system may include a cross-linked polyvinylpyrrolidone (PVP) polymer. The thickening system may also include POLYPLASDONE® XL 10F, which is commercially available from Ashland Inc. of Covington, Ky. Additional illustrative thickeners may include, but are not limited to, carbomers (e.g., carboxyvinyl polymers), carrageenans (e.g., Irish moss, carrageenan, iota-carrageenan, etc.), high molecular weight polyethylene glycols (e.g., CARBOWAX®, which is commercially available from The Dow Chemical Company of Midland, Mich.), cellulosic polymers, hydroxyethylcellulose, carboxymethylcellulose, and salts thereof (e.g., CMC sodium), natural gums (e.g., karaya, xanthan, gum arabic, and tragacanth), colloidal magnesium aluminum silicate, hydrophilic polymers, such as carbomers, such as carboxymethylene polymers, such as acrylic acid polymers, and acrylic acid copolymers, and the like, and mixtures or combinations thereof. Carboxypolymethylene is a slightly acidic vinyl polymer with active carboxyl groups. One such carboxypolymethylene is CARBOPOL® 974 and/or 980, commercially available from Noveon, Inc. of Cleveland, Ohio. In at least one implementation, the one or more thickeners may be or include a cellulose ether, selected from one or more of hydroxyalkyl cellulose polymers, such as hydroxypropyl methyl cellulose (HPMC), hydroxypropyl cellulose, hyrdoxyethyl cellulose, methyl cellulose, ethylcellulose, carboxymethyl cellulose, and mixtures or combinations thereof.

In at least one implementation, the thickening system may include a single thickener. For example, the thickening system may include the cross-linked polyvinylpyrrolidone (PVP) polymer. In another implementation, the thickening system may include a plurality of thickeners. For example, the thickening system may include the cross-linked PVP polymer and a silica thickener. In another example, the thickening system may include a plurality of silica thickeners.

The amount or concentration of the thickening system and/or the thickeners thereof present in the oral care product or the film forming composition thereof may vary widely. The amount of the thickening system and/or the thickeners thereof present in the oral care product or the film forming composition thereof may be from about 10 wt % to about 30 wt % based on the total weight of the oral care product or the film forming composition thereof. For example, the amount of the thickening system and/or the thickeners thereof present in the oral care product or the film forming composition thereof may be from about 10 wt %, about 11 wt %, about 12 wt %, about 13 wt %, about 14 wt %, about 15 wt %, about 16 wt %, about 17 wt %, about 18 wt %, about 19 wt %, about 20 wt %, or about 21 wt % to about 22 wt %, about 23 wt %, about 24 wt %, about 25 wt %, about 26 wt %, about 27 wt %, about 28 wt %, about 29 wt %, or about 30 wt %. In another example, the amount of the thickening system and/or the thickeners thereof present in the oral care product or the film forming composition thereof may be from about 12 wt % to about 30 wt %, about 13 wt % to about 29 wt %, about 14 wt % to about 28 wt %, about 15 wt % to about 27 wt %, about 16 wt % to about 26 wt %, about 17 wt % to about 25 wt %, about 18 wt % to about 24 wt %, about 19 wt % to about 23 wt %, or about 20 wt % to about 22 wt %. In a typical implementation, the amount of the thickening system and/or the thickeners thereof present in the oral care product or the film forming composition thereof may be from about 20 wt % to about 22 wt %, more typically about 21 wt %.

Flavoring Agents

The film forming composition may also include one or more flavoring agents. Illustrative flavoring agents that may be utilized in the film forming composition may be or include, but are not limited to, essential oils and various flavoring aldehydes, esters, alcohols, and similar materials, as well as sweeteners such as sodium saccharin, and the like, and mixtures or combinations thereof. Illustrative essential oils may include, but are not limited to, oils of spearmint, peppermint, wintergreen, sassafras, clove, sage, eucalyptus, marjoram, cinnamon, lemon, lime, grapefruit, and orange. Also useful are chemicals such as menthol, carvone, anethole, and the like, and mixtures or combinations thereof. In a preferred implementation, the flavoring agents include oils of peppermint and spearmint.

The amount or concentration of the one or more flavoring agents present in the oral care product or the film forming composition thereof may vary widely. In at least one implementation, the amount of the one or more flavoring agents present may be from about 0.01 weight % to about 50 weight %, based on a total weight of the oral care product or the film forming composition thereof. For example, the amount of the one or more flavoring agents present may be from about 0.01 weight %, about 1 weight %, about 5 weight %, about 10 weight %, about 15 weight %, about 20 weight %, or about 25 weight % to about 30 weight %, about 35 weight %, about 40 weight %, about 45 weight %, or about 50 weight %.

Orally Acceptable Vehicle

In at least one implementation, the film forming composition may be dispersed or dissolved in an orally acceptable vehicle. As used herein, the expression "orally acceptable vehicle" may refer to a suitable vehicle, ingredient, or combination of ingredients, which can be used to form and/or apply the film forming composition or one or more components thereof to surfaces of the oral cavity in a safe and effective manner. For example, the orally acceptable vehicle may be a suitable solvent, and the film forming composition may be dispersed, dissolved, mixed, or otherwise contacted with the suitable solvent to prepare or form the oral care product. Illustrative solvents may be or include, but are not limited to, ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, benzyl alcohol, or the like, and mixtures or combinations thereof. In a preferred implementation, the orally acceptable vehicle is ethanol.

The orally acceptable vehicle may make up the balance of the oral care product. In at least one implementation, the orally acceptable vehicle (e.g., ethanol) may be present in an amount of at least 60 weight %, at least 62 weight %, at least 64 weight %, at least 66 weight %, at least 68 weight %, at least 70 weight %, at least 72 weight %, at least 74 weight %, at least 76 weight %, at least 78 weight %, at least 80 weight %, at least 82 weight %, at least 84 weight %, at least 86 weight %, at least 88 weight %, at least 90 weight %, at least 92 weight %, at least 94 weight %, at least 96 weight %, at least 98 weight %, or at least 99 weight %, based on a total weight of the oral care product.

Polar Solvent

In various implementations, the film forming composition disclosed herein may include one r more solvents, such as a polar solvent. The polar solvent may be selected such that it is capable of at least partially dissolving the hydrophobic polymers disclosed herein. The polar solvent may include glycerin, propylene glycol, alcohol, or water.

In a preferred implementation, the polar solvent includes ethanol, for example, in an amount sufficient to dissolve the ingredients of the film forming composition, in particular the hydrophobic polymer. In various implementations, the polar solvent may be present in the film forming composition in an amount of up to about 99%, including from greater than about 0% to about 99%, more preferably from about 10% to about 95%, or from about 20% to about 80%, most preferably including an amount of about 79%, by weight relative to the total weight of the film forming composition.

Additional Ingredients

It should be appreciated by one having ordinary skill in the art, that the oral care products and/or the film forming compositions thereof may include other additional ingredients/components. For example, the oral care products and/or the film forming compositions thereof may include desensitizing agents, viscosity modifiers, diluents, surface active agents (e.g., emulsifiers, foam modulators, etc.), pH modifying agents (e.g., acids and bases), humectants, mouth feel agents, sweetening agents, flavor agents, colorants, preservatives, and the like, and combinations and mixtures thereof. It should further be appreciated by one having ordinary skill in the art that while general attributes of each of the above categories of materials may differ, there may be some common attributes and any given material may serve multiple purposes within two or more of such categories of materials.

All ingredients for use in the compositions described herein should be orally acceptable. As used herein, "orally acceptable" may refer to any ingredient that is present in a composition as described in an amount and form that does not render the composition unsafe for use in the oral cavity.

Methods

The present disclosure may provide methods for preventing the formation of caries on surfaces of the oral cavity in a human or animal subject. As used herein "animal subject" may include higher order non-human mammals such as canines, felines, and horses. The method may include contacting any one of the film forming compositions disclosed herein with surfaces of the oral cavity, such as surfaces of teeth. Contacting the surface of the teeth with the film forming composition may include applying the film forming composition directly to the teeth using a delivery device, such as a pen, (e.g., a COLGATE® whitening pen or a COLGATE® ACTIS™ whitening pen, Colgate-Palmolive Company, New York, N.Y.), a liquid stick having an applicator, such as a felt tip, brush, spray, roller ball, or nonwoven pad, or the like. Contacting the surface of the teeth with the film forming composition may also include disposing the film forming composition in a dental tray (e.g., reservoir of a dental tray) and disposing the dental tray about the teeth.

The method may also include evaporating a solvent or orally acceptable vehicle from the film forming composition to form a film on the surfaces of the teeth. The resulting film, formed in situ, may allow suspended fluoride to remain in contact with the surfaces of the teeth. The method may further include the sustained release of fluoride from the film to surfaces of the teeth. The sustained release of fluoride from the film to surfaces of the teeth may include solubilizing the fluoride compound disposed in the film to provide fluoride ions. The fluoride ions may migrate or be delivered to the surfaces of the teeth. The method may also include maintaining the film on the surfaces of the teeth for at least 12 hours, at least one day, at least two days, at least three days, at least four days, or more.

The method may include applying or contacting the oral care product and/or the film forming composition thereof with the surfaces of the teeth at predetermined intervals. For example, the method may include applying or contacting the oral care product and/or the film forming composition thereof with the surfaces of the teeth on a daily basis, every other day, once or twice a week, or once a month. In another example, the method may include applying or contacting the oral care product and/or the film forming composition thereof with the surfaces of the teeth at least once a day, at least once every two days, at least once every three days, at least once every five days, at least once a week, at least once every two weeks, or at least once a month. The oral care product and/or the film forming composition thereof may be utilized for up to 2 weeks, up to 3 weeks, up to 4 weeks, up to 6 weeks, up to 8 weeks, or greater.

The present disclosure may provide methods for preparing a film forming composition. The method may include mixing, dissolving, combining, or otherwise contacting each component of the film forming composition with one another. For example, the method may include contacting an acrylate/octylacrylamide copolymer, a fluoride compound, and an orally acceptable solvent with one another. In another example, the method may include contacting a cellulose derivative, a rosin, and a fluoride compound with one another.

All ingredients for use in the compositions described herein should be orally acceptable. As used herein, "orally acceptable" may refer any ingredient that is present in a composition as described in an amount and form which does not render the composition unsafe for use in the oral cavity.

EXAMPLES

The examples and other implementations described herein are exemplary and not intended to be limiting in describing the full scope of compositions and methods of this disclosure. Equivalent changes, modifications and variations of specific implementations, materials, compositions and methods may be made within the scope of the present disclosure, with substantially similar results.

Example 1

The efficacy of exemplary film forming compositions (1)-(5) for preventing the formation of caries or tooth decay was evaluated in vitro via pH cycling. Particularly, the efficacy of the film forming compositions (1)-(5) on the loss of surface microhardness or surface microhardness loss (SMHL) was evaluated. The test film forming compositions (1)-(5) were prepared by combining the ingredients/components according to Table 1. Particularly, the ingredients/components of each of the test film forming compositions (1)-(5) were combined or otherwise contacted with one another in a spin mix jar and mixed at about 3540 rpms for about 5 minutes until a homogenous suspension was obtained.

TABLE 1

Test Film Forming Compositions

| INGREDIENT/COMPONENT | (1) | (2) | (3) | (4) | (5) |
|---|---|---|---|---|---|
| Acrylates/Octylacrylamide Copolymer | 20% | 20% | — | — | — |
| Ethylcellulose | — | — | 13% | 13% | 13% |
| Hydrogenated Rosin | — | — | 5% | 5% | 5% |
| Sodium Fluoride | 5% | 1.11% | 5% | 1.11% | 0.26% |
| Ethanol | 75% | 78.89% | 77% | 80.89% | 81.74% |
| Total | 100.0 | 100.0 | 100.0 | 100.0 | 100.0 |

To evaluate the efficacy of the film forming compositions (1)-(5), a thin layer of each of the film forming compositions (1)-(5) was brushed onto a respective enamel block and set aside for a time sufficient to allow the ethanol to evaporate. The film forming compositions (1)-(5) were evaluated along with a negative control (N1) and two positive controls (P1) and (P2). The negative control (N1) was an untreated enamel block, and the positive controls (P1) and (P2) were DURAPHAT® and PREVIDENT®, respectively, both of which are commercially available from Colgate-Palmolive Company of New York, N.Y. It should be appreciated that both DURAPHAT® and PREVIDENT® include or contain about 5% of sodium fluoride. Each of the film forming compositions (1)-(5) and the controls (N1), (P1), and (P2) was evaluated in triplicate. As such, three separate enamel blocks were used for each of the film forming compositions (1)-(5) and each of the controls (N1), (P1), and (P2).

After the ethanol was allowed to evaporate, each of the enamel blocks was transferred into a well plate containing 2 mL of a demineralization solution (pH of about 4), which was prepared by combining the ingredients/components according to Table 2, and incubated at about 37° C. for about 55 minutes. Each of the enamel blocks was then washed once in deionized (DI) water and transferred to a well plate containing 2 mL of a remineralization solution (pH of about 7), which was prepared by combining the ingredients/components according to Table 3, and incubated at about 37° C. for about 3 hours. After incubating for 3 hours, each of the enamel blocks was removed from the well plate including the remineralization solution and wiped twice with cotton swabs dipped in ethanol and subsequently dipped in ethanol once. Each of the enamel blocks was then transferred to a new well plate containing 2 mL of the remineralization solution and incubated at about 37° C. overnight for about 16 hours. After incubating, each of the enamel blocks was removed from the remineralization solution, washed in DI water, and transferred into a new well plate containing 2 mL of the demineralization solution and incubated at about 37° C. for about 55 minutes. After demineralization, each of the enamel blocks was washed once with DI water and transferred to a new well plate containing 2 mL of the remineralization solution and incubated at about 37° C. for about 36 hours. After incubation, each of the enamel blocks was removed from the remineralization solution, washed, and subsequently dried on the bench top.

TABLE 2

Demineralization Solution (pH of about 4)

| INGREDIENT/COMPONENT | Mass |
|---|---|
| Calcium Nitrate Tetrahydrate ($Ca(NO_3)_2 \cdot 4H_2O$) | 0.4723 g/L |
| Potassium Phosphate Monobasic ($KH_2PO_4$) | 0.2722 g/L |
| Acetic Acid ($CH_3COOH$) | 4.5083 g/L |

TABLE 3

Remineralization Solution (pH of about 7)

| INGREDIENT/COMPONENT | Mass |
|---|---|
| Calcium Nitrate Tetrahydrate ($Ca(NO_3)_2 \cdot 4H_2O$) | 0.3542 g/L |
| Potassium Phosphate Monobasic ($KH_2PO_4$) | 0.1225 g/L |
| Potassium Chloride (KCl) | 9.6915 g/L |
| Phosphate Buffered Saline (PBS) | 100 mL/L |

After drying, the mechanical properties of each of the enamel blocks were evaluated using a MICROMET® 5010 Micro-indentation Hardness Tester, which is commercially available from Thermo Fisher Scientific of Waltham, Mass. The MICROMET® 5010 Micro-indentation Hardness Tester was prepared with a Knoop Diamond Indenter at a 25 g load, and 5 indentations were taken for each of the enamel blocks. The surface microhardness loss (SMHS) of each of the enamel blocks was calculated according to Formula 1. The calculated SMHS % are summarized in Table 4. It should be appreciated that the lower the SMHL % value, the greater the anti-caries effect or the greater the efficacy for preventing caries or tooth decay.

$$SMHL\ \% = \frac{Microhardness\ Effect@Baseline - Microhardness\ Effect\ after\ pH\ Cycling}{Microhardness\ Effect@Baseline} \quad (1)$$

TABLE 4

SMHL % of Test Film Forming Compositions (1)-(5) and Controls (N1), (P1), and (P2)

| | (N1) | (P1) | (P2) | (1) | (2) | (3) | (4) | (5) |
|---|---|---|---|---|---|---|---|---|
| SMHL (%) | 56.23 | 29.23 | 25.45 | 17.74 | 16.67 | 22.29 | 12.60 | 18.71 |
| Standard Deviation | 5.86 | 0.12 | 1.33 | 5.68 | 4.54 | 3.83 | 3.75 | 1.45 |

As indicated in Table 4, each of the test film forming compositions (1)-(5) exhibited comparable or relatively greater anti-caries effect; and thus, exhibited comparable or greater efficacy for preventing caries or tooth decay. It was surprisingly and unexpectedly discovered that the test film forming compositions (1)-(5) exhibited relatively greater anti-caries effect even at lower concentrations of sodium fluoride.

Example 2

The ability or efficacy of films formed from varying film forming compositions to resist acid erosion on surfaces of the oral cavity (e.g., surfaces of teeth) was evaluated in vitro. Particularly, the efficacy of a film forming composition (6) on the loss of surface microhardness or surface microhardness loss (SMHL) was evaluated. The test film forming composition (6) was prepared by combining the ingredients/components according to Table 5. Specifically, the ingredients/components were combined or otherwise contacted with one another in a spin mix jar and mixed at about 3540 rpms for about 5 minutes until a homogenous suspension was obtained.

TABLE 5

Test Film Forming Compositions (1)-(5)

| INGREDIENT/COMPONENT | (6) |
|---|---|
| Acrylates/Octylacrylamide Copolymer | 20% |
| Ethanol | 80% |
| Total | 100.0 |

To evaluate the efficacy of the film forming composition (6), a think layer of the film forming composition (6) was brushed onto an enamel block and set aside for a time sufficient to allow the ethanol to evaporate. A negative control was provided by an uncoated enamel block. After the ethanol was allowed to evaporate, each of the enamel blocks was transferred to a well plate containing 2 mL of the demineralization solution prepared in Example 1 and incubated at about 37° C. for about 30 minutes. Each of the enamel blocks was then washed thoroughly with DI water and allowed to dry.

After drying, the mechanical properties of each of the enamel blocks were evaluated using a MICROMET® 5010 Micro-indentation Hardness Tester, which is commercially available from Thermo Fisher Scientific of Waltham, Mass. The MICROMET® 5010 Micro-indentation Hardness Tester was prepared with a Knoop Diamond Indenter at a 25 g load, and 5 indentations were taken for each of the enamel blocks. The surface microhardness loss (SMHS) of each of the enamel blocks was calculated according to Formula 1. The calculated SMHS % are summarized in Table 6. It should be appreciated that the lower the SMHL % value, the greater the anti-erosion efficacy of the film.

TABLE 6

SMHL % of Test Film Forming Composition (6) and Control (N2)

|  | (N2) | (6) |
|---|---|---|
| SMHL (%) | 92% | 0% |

As illustrated in Table 6, the film formed from the film forming composition (6) completely protected the enamel block, or surfaces of the teeth, from acid erosion.

The present disclosure has been described with reference to exemplary implementations. Although a limited number of implementations have been shown and described, it will be appreciated by those skilled in the art that changes may be made in these implementations without departing from the principles and spirit of the preceding detailed description. It is intended that the present disclosure be construed as including all such modifications and alterations insofar as they come within the scope of the appended claims or the equivalents thereof.

What is claimed is:

1. A film forming composition for preventing the formation of caries on teeth, the film forming composition consisting of:
   one or more acrylate/octylacrylamide copolymers;
   one or more fluoride compounds; and
   one or more orally acceptable solvents.

2. The film forming composition of claim 1 wherein
   the one or more fluoride compounds comprise sodium fluoride; and
   the one or more orally acceptable solvents comprise ethanol.

3. The film forming composition of claim 1, wherein the one or more acrylate/octylacrylamide copolymers are selected from the group consisting of copolymers of 2-propenoic acid, 2-methyl-, 2-methylpropyl ester, and polymers with 2-propenoic acid and N-(1,1,3,3-tetramethylbutyl)-2-propenamide.

4. The film forming composition of claim 1, wherein the fluoride compound is a soluble salt of a fluoride ion.

5. The film forming composition of claim 4, wherein the fluoride compound comprises one or more of sodium fluoride, potassium fluoride, calcium fluoride, zinc fluoride, zinc ammonium fluoride, lithium fluoride, ammonium fluoride, stannous fluoride, and stannous fluorozirconate.

6. The composition of claim 5, wherein the fluoride compound comprises sodium fluoride.

7. The film forming composition of claim 1, wherein the orally acceptable solvent comprises one or more of ethanol, methanol, isopropanol, butanol, water, acetone, methyl ethyl ketone, ethyl acetate, butyl acetate, cyclohexanone, cyclohexane, methylene chloride, chloroform, carbon tetrachloride, trichloroethylene, perchloroethylene, methyl glycol acetate, toluene, benzene, diethyl ether, and benzyl alcohol.

8. The composition of claim 7, wherein the orally acceptable solvent comprises ethanol.

9. The composition of claim 1, wherein the one or more acrylate/octylacrylamide copolymers are present in an amount of from 15% to 30% by weight of the composition.

10. A method for preparing the film forming composition of claim 1, the method comprising contacting the acrylate/octylacrylamide copolymer, the fluoride compound, and the orally acceptable solvent with one another.

11. A method for preventing acid erosion on surfaces of teeth, the method comprising: contacting the surfaces of the teeth with the film forming composition of claim 1.

12. A method for preventing the formation of caries on teeth, the method comprising: contacting the teeth with the film forming composition of claim 1.

* * * * *